United States Patent [19]
Dempsey et al.

[11] Patent Number: 6,132,371
[45] Date of Patent: Oct. 17, 2000

[54] LEADLESS MONITORING OF PHYSIOLOGICAL CONDITIONS

[75] Inventors: Michael K. Dempsey, Westford; Susan J. Kohler, Concord, both of Mass.

[73] Assignee: Hewlett-Packard Company, Palo Alto, Calif.

[21] Appl. No.: 09/082,094

[22] Filed: May 20, 1998

[51] Int. Cl.$^7$ ........................................... A61B 5/00
[52] U.S. Cl. ............................................. 600/300
[58] Field of Search ................................. 600/300, 317; 128/630, 668, 696, 670, 653, 671

[56] References Cited

U.S. PATENT DOCUMENTS

| | | | |
|---|---|---|---|
| 4,635,296 | 1/1987 | Dinsmore | 455/113 |
| 4,827,943 | 5/1989 | Bornn et al. | 128/688 |
| 5,322,034 | 6/1994 | Willham et al. | 600/300 |
| 5,445,150 | 8/1995 | Dumoulin et al. | 128/653.1 |
| 5,499,626 | 3/1996 | Willham et al. | 600/300 |
| 5,704,352 | 1/1998 | Tremblay et al. | 128/630 |

OTHER PUBLICATIONS

California Institute of Technology, Jet Propulsion Laboratory, 9 pages, first page includes "Phase I: Develop Proof of Concept; Phase II: Prepare and Field Test a Prototype Model; Phase III: Assist in the Development of the Commercial Prototype System and Assist in an Installation in a Local Jail Facility" (date unknown).

California Institute of Technology, Jet Propulsion Laboratory Technology Report, 19 pages, "Person–Locater System Based on Wristband Radio Transponders" (Dec., 1995).

Ishak, Waguih S. et al., "Surface–Acoustic–Wave Delay Lines and Transversal Filters," Hewlett Packard Journal, pp. 3–27 (Dec., 1981).

NASA Tech Briefs (MSC–21501), 15 pages, "Biomedical Telectrodes" (1988).

Viewgraphs re: Backscatter Technology, 18 pages, first page titled "Infostation System Architecture," private communication from Wireless Information Network Laboratory (WINLAB), Rutgers University, NJ (date unknown).

Johnston, Ronald H. et al., University of Calgary, "A Biotelemetry System for Monitoring Heart Rates in Unrestrained Ungulates," Biotelemetry Patient Montig 7, pp 188–198 (1980).

Seals J. et al., Georgia Institute of Technology, 8 pages, "An Electromagnetic–Based Non–Contact Vital Signs Monitor," (date unknown).

Sugiura, T. et al., "Microcomputer–Based Telemetry System for Heart Rate and Blood Temperature in Dogs," pp. 551–567 (date unknown).

*Primary Examiner*—Max Hindenburg
*Assistant Examiner*—Brian Szmal

[57] ABSTRACT

A signal representing a physiological condition of a patient is used to modulate an electromagnetic signal received by a transponder so that a modulated electromagnetic signal representative of the signal is re-radiated by the transponder. The transponder includes an antenna and a diode coupled between the antenna and ground. Changing states of a digital signal from an analog-to digital converter that receives an input from a physiological transducer cause the diode to selectively conduct, which causes the impedance of the antenna to change accordingly. The re-radiated electromagnetic signal is demodulated to recover the digital signal, and the output signal of the transducer is recovered and may be displayed to a user and otherwise processed and/or stored.

25 Claims, 3 Drawing Sheets

LEADLESS MONITORING OF PHYSIOLOGICAL CONDITIONS

BACKGROUND OF THE INVENTION

1. Field of the Invention

The present invention is directed to the monitoring of physiological conditions of patients and, more particularly, to the leadless monitoring of such conditions.

2. Discussion of Related Art

In modern medicine, to properly diagnose and treat a patient, it is essential that health care providers have the ability to monitor various physiological conditions of the patient. Therefore, many electronic devices have been developed that monitor various physiological conditions. Examples of such devices include electrocardiograph (ECG) monitors, electroencephalographs (EEGs), blood oxygenation ($SpO_2$) monitors, etc., as well as monitors that measure various combinations of the physiological conditions monitored by each of these devices.

Conventional patient monitoring devices generally employ one or more transducers to generate electronic signals indicative of physiological conditions of a patient, and use separate electronic units to receive these electronic signals and display such conditions to clinicians. These monitoring devices typically use cables to transmit the electronic signals from the transducer(s) to the display devices. For example, a conventional ECG monitor may employ five separate ECG electrodes to monitor ECG activity and use five separate cables to communicate the electronic signals from the electrodes to a bedside monitoring device. The use of such cables and the resulting "cable clutter," however, present numerous problems and disadvantages for the patients, the health care providers, and the monitoring systems themselves.

Such problems and disadvantages include, for example: (a) the use of cables makes the patient uncomfortable by restricting the patient's movement, (b) as the patient moves, electrical artifact can be generated on the cables that can trigger false alarms, (c) the cables must be made of high quality, expensive material so that they can withstand defibrillation, (d) because the cables establish a galvanic connection between the patient and the monitoring device, the patient must be isolated from the electrical mains of the monitoring device via bulky and expensive isolation circuitry, (e) cables can become tangled, damaged by other devices, or damage instruments by pulling them to the floor, (f) connecting and disconnecting cables to/from a patient to permit the patient to move can be quite burdensome, (g) the cables tend to pull on the transducers and frequently are dislodged from them, thereby causing false alarms, and (h) the cables must be cleaned, or even sterilized, each time they are to be used.

In the past, attempts have been made to minimize patient discomfort by "dressing" the cables and to increase the mobility of patients by making the cables as long as possible. Efforts also have been made to bundle sets of several cables, e.g., sets of three to five wires from ECG transducers, into single "trunk cables" in order to minimize the cable clutter near patients. In addition, in certain extreme situations, it has been the practice to restrain the patient physically to reduce the occurrence of one or more of the problems noted above.

Another prior art solution to the above-identified problems is to employ a telemetry transmitter located near the patient to transmit information acquired by physiological transducer(s) to a receiver, e.g., a receiver located at a centrally-located nurses station, that processes, analyzes and/or possibly displays the acquired information. A typical telemetry transmitter is battery operated and may be approximately the size of a bar of soap. Generally, one or more cables are connected between the physiological transducer(s) attached to the patient and the telemetry transmitter.

While telemetry transmitters tend to be significantly smaller and less expensive than bedside monitoring devices, these transmitters still are relatively burdensome to the patient since the patient is forced to carry the transmitter. It is primarily the transmitter portion of a telemetry transmitter and the batteries required to operate it that make the device relatively bulky. Because a telemetry transmitter must generate and transmit an RF signal, it consumes a significant amount of power. The charge level of the batteries of a telemetry transmitter therefore need to be evaluated frequently.

In addition, the cables used in connection with a telemetry transmitter pose many of the same problems identified above regarding the cables used with bedside monitoring devices. Further, because of the relatively high cost and fragile nature of telemetry transmitters, it is impractical in many situations to provide each patient with a separate device.

What is needed, therefore, is an improved device and method for monitoring the physiological conditions of patients.

SUMMARY OF THE INVENTION

According to one aspect of the present invention, a device for monitoring a physiological condition of a patient includes a transducer and a transponder. The transducer is adapted to sense the physiological condition of the patient and to produce an output signal indicative of the sensed condition. The transponder is arranged to receive an electromagnetic signal and to re-radiate the electromagnetic signal, wherein the reradiated electromagnetic signal is modulated by a signal representative of the output signal of the transducer.

According to an additional aspect of the invention, the device may include an analog-to-digital converter (ADC) having an analog input coupled to an output of the transducer and a digital output coupled to the transponder to provide the transponder with the signal representative of the output signal of the transducer.

According to yet another aspect of the invention, the transponder may include an antenna and a diode coupled to the antenna. The diode is arranged to selectively conduct responsive to a state of the signal from the digital output of the ADC.

According to another aspect of the present invention, a system for monitoring a physiological condition of a patient includes a transmitter, a transducer, a transponder, and a receiver. The transmitter is configured to emit an electromagnetic signal. The transducer is adapted to sense the physiological condition of the patient and to produce an output signal indicative the condition. The transponder arranged to receive the electromagnetic signal emitted by the transmitter and to re-radiate the electromagnetic signal, wherein the reradiated electromagnetic signal is modulated by a signal representative of the output signal of the transducer. Finally, the receiver is configured to receive the electromagnetic signal re-radiated by the transponder.

According to another aspect of the present invention, a method for monitoring a physiological condition of a patient is provided in which a physiological condition of the patient is sensed and an output signal indicative of the condition is produced. An electromagnetic signal is received and is modulated in response to a signal representing the output signal. The modulated electromagnetic signal is re-radiated.

According to yet another aspect of the invention, a method for monitoring a physiological condition of a patient is provided in which a transmitter is used to transmit an electromagnetic signal and a physiological condition of a patient is sensed to produce an output signal indicative of the condition. A wireless device, which is distinct from the transmitter, is used to receive the electromagnetic signal from the transmitter, and the electromagnetic signal so received is modulated in response to the output signal. The wireless device is used to re-radiate the modulated electromagnetic signal and the re-radiated electromagnetic signal is received by a receiver, which is distinct from the wireless device.

According to an additional aspect of the invention, the received re-radiated electromagnetic signal may be demodulated, and the demodulated electromagnetic signal may be used to generate a visual representation of the physiological condition or may be otherwise processed or analyzed.

DETAILED DESCRIPTION OF THE INVENTION

Figure 1:
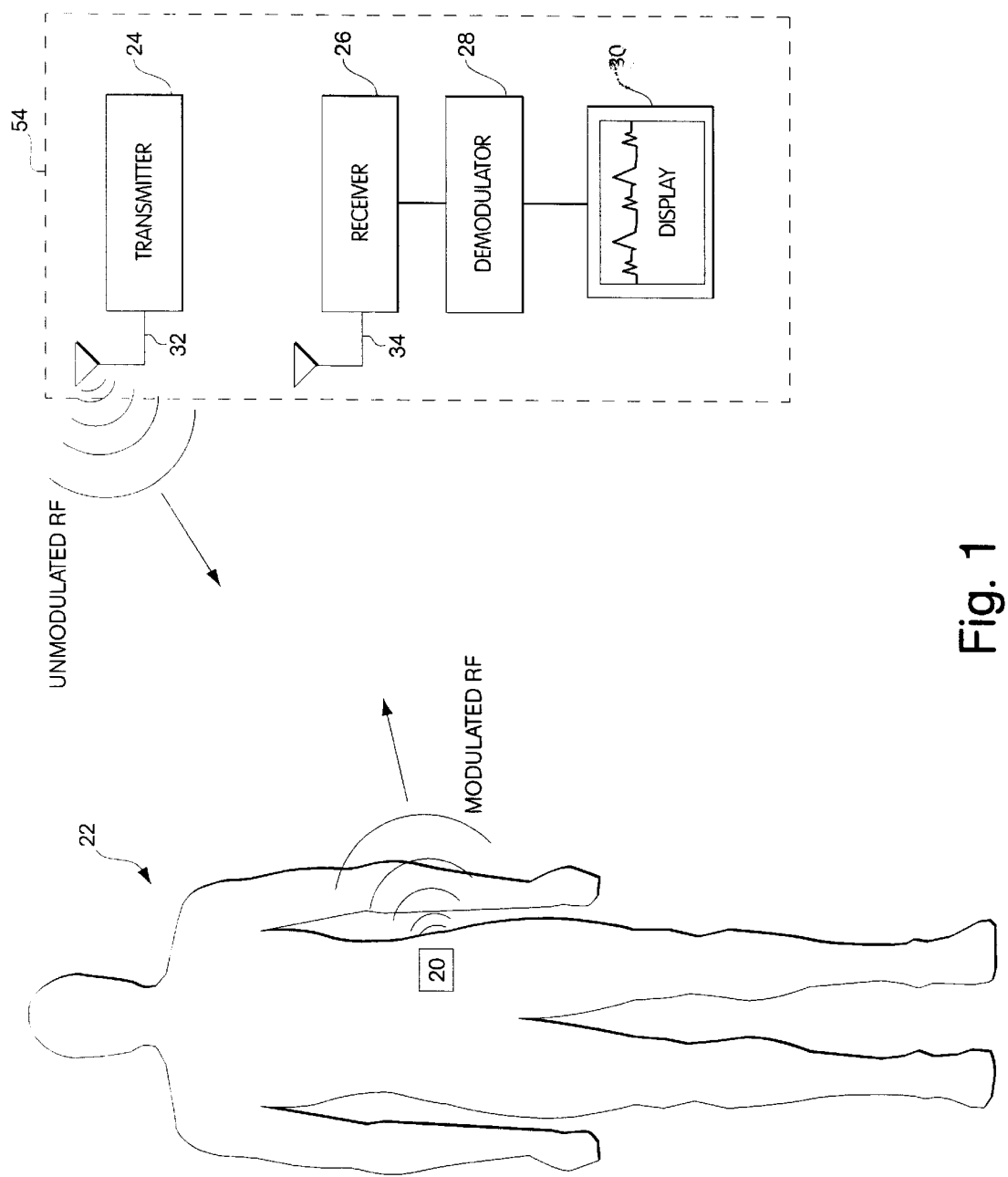
FIG. 1 is a block diagram showing one implementation of the present invention.
Figure 2:
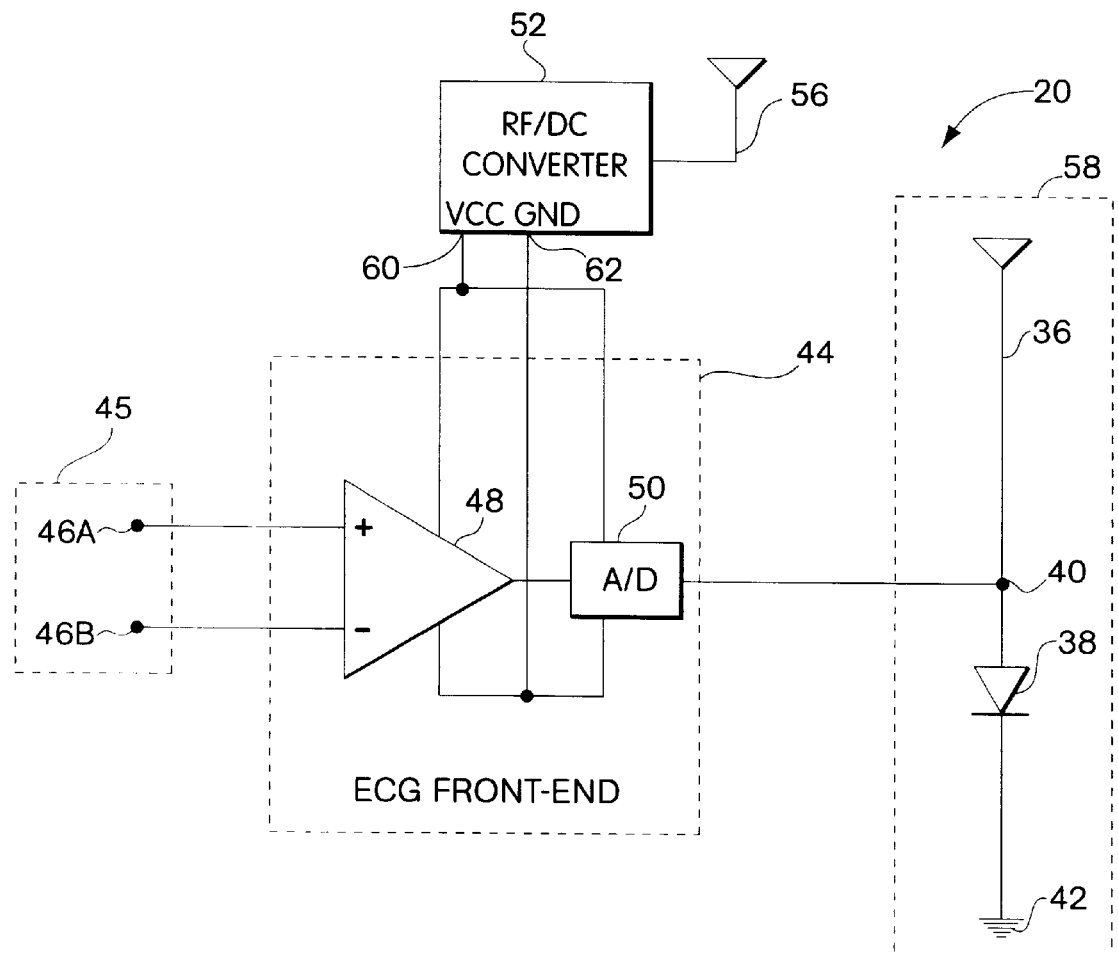
FIG. 2 is a partial schematic/partial block diagram showing in more detail the leadless monitoring device shown in FIG. 1.

FIG. 1 shows an exemplary embodiment of the present invention. As shown, a leadless monitoring device 20, which is described in more detail below in connection with the description of FIG. 2, is arranged to sense a physiological condition of a patient 22. According to one embodiment, most of the components of leadless monitoring device 20 are included within a package that is approximately the size of a conventional ECG electrode, e.g., less than one inch in diameter and less than one-eighth of an inch thick, and is attached to patient 22 in a similar manner as an ECG electrode. Leadless monitoring device therefore may be used without significantly discomforting patient 22.

Also shown in FIG. 1 is a patient monitoring system 54, which includes a transmitter 24, a receiver 26, a demodulator 28, and a display 30. Patient monitoring system 54 communicates with leadless monitoring device 20 via electromagnetic (EM) waves, preferably in the radio-frequency (RF) range, as explained below. Patient 22 therefore may move about freely in the general vicinity of transmitter 24 and receiver 26.

Transmitter 24 is configured to emit an RF signal via an antenna 32. As shown in FIG. 1, transmitter 24 and antenna 32 are arranged such that a portion of the RF energy emitted by antenna 32 radiates in the general direction of leadless monitoring device 20. According to one embodiment, transmitter 24 may be any simple continuous-wave (CW) signal generator. For example, transmitter 24 may include a signal generator such as model number HP 8656B manufactured by Hewlett-Packard Company. According to an exemplary implementation, transmitter 24 may be configured to emit an RF signal at a selected frequency between 300 and 900 megahertz (MHZ) and at a power level between −10 dBm and +10 dBm. The frequency and power level of the electromagnetic signal emitted by transmitter 24 are not critical, however. The only constraint on these settings is that the method, frequency and power level be such that the signal-to-noise ratio of the RF signal received by antenna 34 (described below) is sufficient to recover information modulated onto the RF signal by leadless monitoring device 20, as explained below.

Leadless monitoring device 20, shown and described in more detail below, receives the RF signal emitted by transmitter 24 and re-radiates the RF signal such that information generated by the physiological transducer (included in leadless monitoring device 20) modulates the re-radiated RF signal. In one embodiment, this information is a digital data stream representing the amplitude of a potential difference measured by a pair of ECG electrodes, and the amplitude of the re-radiated RF signal is modulated according to state changes of the digital bit-stream, i.e., it is an amplitude-modulated (AM) signal. It should be appreciated, however, that the re-radiated RF signal may be mixed with an analog signal representing a physiological condition to produce a frequency-modulated (FM) signal, may be modulated using known phase-modulation (PM) techniques, or may be modulated in any other manner known to those skilled in the art. Such embodiments are intended to be within the scope of the present invention.

Receiver 26 is configured to receive, via antenna 34, the RF signal re-radiated by leadless monitoring device 20. According to an alternative embodiment, antennas 32 and 34 may be replaced with a single antenna and this antenna may be coupled to transmitter 24 and receiver 26 through a mixer.

Demodulator 28 is coupled to receiver 26 and is configured to demodulate the RF signal received by receiver 26 to recover the information modulated onto the RF signal by leadless monitoring device 20. Display 30 is coupled to demodulator 28 and displays the information recovered by demodulator 28. It should be appreciated that display 30 is only an example of a device that could make use of the output signal of demodulator 28 and that other devices also may use this signal for other useful purposes. For example, a central nurse station may analyze the output signal of demodulator 28 to detect anomalies in the physiological condition of a patient and generate alarms in response to the detection of such anomalies. Alternatively, the signal may be processed so as to extract useful information and such information may be logged into a database at a central location.

According to one embodiment of the invention, receiver 26, demodulator 28 and display 30 all are included in an RF Communications Test Set, e.g., model number HP8920A manufactured by Hewlett-Packard Company. According to an exemplary implementation, the HP8920A Test Set may be set to operate in Duplex mode, and may be configured for AM demodulation with an intermediate frequency (IF) bandwidth of 230 kilohertz (kHz).

FIG. 2 shows an exemplary embodiment of leadless monitoring device 20. As shown, leadless monitoring device 20 includes a physiological transducer 45 (including a pair of ECG electrodes 46A and 46B), an ECG front-end 44, an RF-to-DC converter 52, and a transponder 58. Transducer 45 and ECG front-end 44 are well known to those skilled in the art. Each of ECG electrodes 46A and 46B may include a cloth patch, approximately one inch in diameter, having an adhesive substance on one side to permit it to be attached to a patient. A small metal button adapted to have another metal fastener mate with the button may be attached to the patch, and a gel substance may be placed on the same side of the patch as the adhesive to provide conductivity between the button and the skin of the patient.

According to one embodiment, ECG front-end 44, RF-to-DC converter 52 and transponder 58 all may be included on the non-adhesive surface of one of the pair of ECG electrodes 46A and 46B, and a wired lead from the other (standard) electrode may be fed to the electrode having the active components on it. This device is only slightly larger than the electrodes themselves. Because this embodiment of leadless monitoring device 20 may be constructed at a minimal cost, it may be disposed of after being used on a single patient. Therefore, in such an embodiment, sterilization of the devices need not be a concern.

In the example shown in FIG. 2, ECG front-end 44 includes a differential amplifier 48 and an analog-to-digital converter (ADC) 50. As shown, an output of amplifier 48 feeds an analog input of ADC 50. According to one embodiment, ADC 50 includes a 12 bit delta-sigma ADC preceded by an antialiasing filter.

The active components of leadless monitoring device 20, i.e., amplifier 48 and ADC 50, are powered from DC outputs 60 and 62 of RF-to-DC converter 52, which is described in more detail below. It should be understood, however, that any other power source, e.g., a battery may be used to provide power to active components of ECG front-end 44. Alternatively, an ECG front-end using only passive components may be employed, in which case a power source such as RF-to-DC converter 52 is unnecessary.

As shown in FIG. 2, transponder 58 includes an antenna 36 and a diode 38. A digital output of ADC 50 is connected to a node 40, which is a connection point of antenna 36 and the anode of diode 38. The cathode of diode 38 is connected to a ground node 42. According to one embodiment, diode 38 is a zero-bias diode, e.g., model number HP5802 manufactured by Hewlett-Packard Company, and antenna 36 is a thirty-three centimeter (cm) end-fed monopole antenna. The ideal length of antenna 36, however, is dependent on the frequency at which transmitter 24 (shown in FIG. 1) is operating. That is, antenna 36 ideally should be approximately one-fourth as long as a wavelength of an RF wave from transmitter 24 (shown in FIG. 1). It should be appreciated, however, that this antenna/diode implementation of transponder 58 is only one example of a transponder that may be employed according to the invention, and any other transponder arrangement that performs a similar function alternatively may be employed. For example, a one-half wave center-fed dipole with a diode interposed between its two end nodes may be used instead of the monopole antenna shown in FIG. 2.

According to an exemplary embodiment, antenna 36 constitutes the outer conductor of a coaxial cable extending between a first ECG electrode, e.g., ECG electrode 46A, and a second ECG electrode, e.g., ECG electrode 46B, on which ECG front-end 44, RF-to-DC converter 52 and transponder 58 are mounted. The inner conductor of this coaxial cable may be used to carry an electronic signal from the first ECG electrode to one of the inputs of ECG front end 44 (mounted on the second ECG electrode).

ECG electrodes 46A and 46B of transducer 45 are connected to opposite polarity inputs of differential amplifier 48. Therefore, the differential voltage between electrodes 46A and 46B determines the serial digital output stream of ADC 50. Because diode 38 is connected between the output of ADC 50 and ground, when the output of ADC 50 is in a high state, e.g., is at approximately two volts, diode 38 is turned on, and when the output of ADC 50 is in a low state, e.g., is at zero volts, diode 38 is turned off. This turning on and off of diode 38, in turn, affects the impedance of antenna 36 so that a significantly greater portion of any RF energy received by antenna 36 is re-radiated (i.e., reflected) by transponder 58 when diode 38 is turned off than when it is turned on. In other words, when diode 38 is turned on, a large portion of the RF energy received by antenna 36 will be shunted to ground node 42.

Thus, in the embodiment of FIG. 2, the RF signal re-radiated by transponder 58 is modulated (i.e., its amplitude is modulated) by a signal (i.e., the digital bit-stream output by ADC 50) representing an output signal of a physiological transducer (i.e., a differential voltage sensed between ECG electrodes 46A and 46B). With regard to the particular signals employed in this embodiment, however, it should be appreciated that: (1) the RF signal may be in any suitable frequency range, (2) the RF signal re-radiated by transponder 58 may be modulated using any known modulation technique, (3) the signal representing the output signal of transducer 45 need not be digital, and may include the output signal of the transducer itself, e.g., when FM modulation of the re-radiated RF signal is employed, and (4) transducer 45 may be any device(s) known to those skilled in the art for generating a signal indicative of a physiological condition.

In the embodiment shown, transponder 58 receives and re-radiates the RF signal from transmitter 24 at the same frequency. Those skilled in the art will appreciate, however, that a frequency shifting circuit, e.g., a frequency divider or doubler circuit, may be used within leadless monitoring device 20 so that the frequency of the RF signal re-radiated from transponder 58 is different from the received frequency. According to the invention, it is important only that the carrier component of the RF signal re-radiated by transponder 58 be generated in response to the received RF signal.

Figure 3:
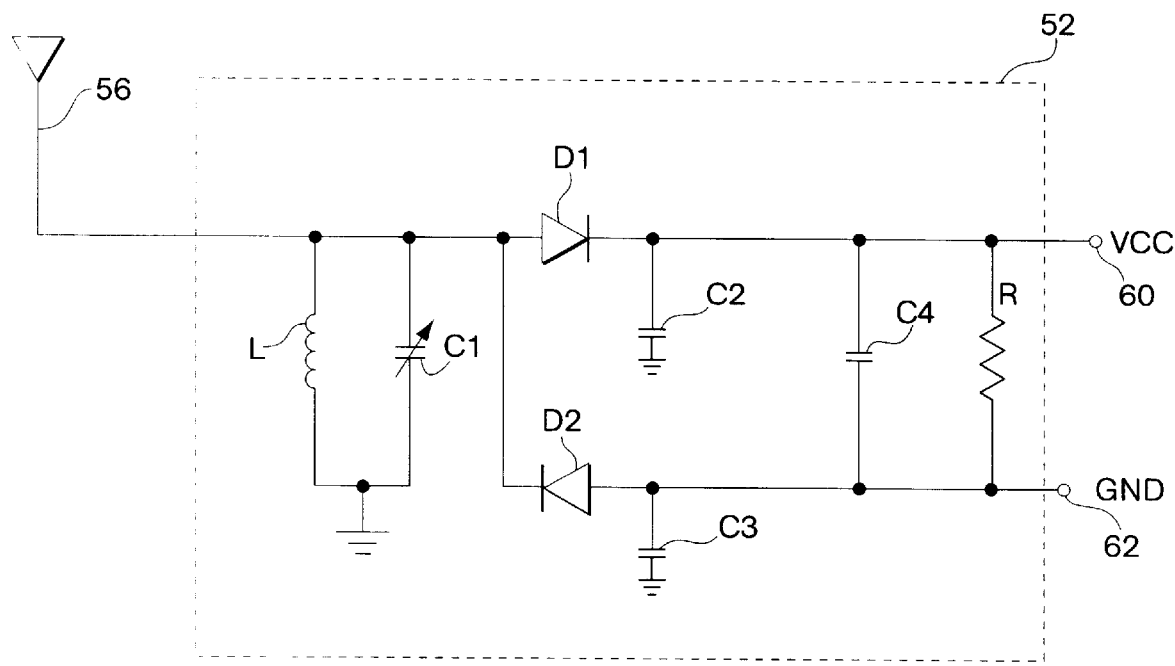
FIG. 3 is a schematic diagram showing in more detail the RF-to-DC converter shown in FIG. 2.

FIG. 3 shows a schematic diagram of one embodiment of RF-to-DC converter 52. As shown, RF-to-DC converter circuit 52 includes an inductor L and a capacitor C1 connected in parallel. One end of these parallel-connected input devices (L and C1) is connected to the end of a half-wave single-end fed antenna 56, and the other end is connected to ground. Capacitor C1 is variable to permit the circuit to be tuned to adjust the RF signal frequency range to which the device is sensitive. Each of diodes D1 and D2 is connected (in an opposite polarity) to the end of antenna 56 so that any received RF signal that passes the input devices L and C1 is half-wave rectified by them. Capacitors C2 and C3 are connected between ground and diodes D1 and D2, respectively, and storage capacitor C4 and resistor R are parallel-connected between the non-grounded electrodes of capacitors C2 and C3, to integrate and store the rectified one-half wave signals from diodes D1 and D2. The charge stored on capacitor C4 then may be used to drive DC power supply leads 60 and 62. As shown in FIG. 2, power supply leads 60 and 62 may be used to power active components of ECG front-end 44, e.g., amplifier 48 and ADC 50.

According to an alternative embodiment, antenna 56 and antenna 58 may constitute the same antenna, instead of each of them constituting separate antennas as shown in FIGS. 2 and 3.

It should be appreciated that the embodiment of RF-to-DC converter 52 shown in FIG. 3 is merely exemplary of the many circuits known to those skilled in the art for converting an RF signal to DC power. In addition, as mentioned above, any other power source, such as a battery, may be employed to provide power to active components of leadless monitoring device 20, or leadless monitoring device 20 may use only passive components (eliminating completely the need for a power source) without departing from the scope of the invention.

The apparatus described herein overcomes many of the drawbacks and disadvantages of prior art patient monitoring systems. Because the apparatus attached to the patient does not require a battery-operated transmitter, it is significantly less bulky, lighter and less costly than prior art telemetry units. Additionally, because the apparatus is wireless, cable-clutter is reduced dramatically over prior art cable-connected monitoring systems, thereby reducing or eliminating the above-noted drawbacks of such systems. Hence, a light-weight, low-cost, and reliable device is provided for monitoring the physiological condition(s) of patients.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A device for monitoring a physiological condition of a patient, comprising:
    a transducer adapted to sense the physiological condition of the patient at a location external to the patient's body and to produce an output signal indicative thereof;
    at least one transducer carrier, supporting the transducer, adapted to be secured to an external surface of the patient's skin; and
    a transponder arranged to wirelessly receive an electromagnetic signal and to re-radiate the electromagnetic signal, wherein the re-radiated electromagnetic signal is modulated in response to the output signal of the transducer.

2. The device as claimed in claim 1, further comprising an analog-to-digital converter (ADC) having an analog input coupled to an output of the transducer and a digital output coupled to the transponder to provide the transponder with a digital signal representative of the output signal of the transducer.

3. The device as claimed in claim 2, wherein the transponder includes an antenna and a diode coupled to the antenna, the diode being arranged to selectively conduct responsive to a state of the digital signal from the digital output of the ADC.

4. The device as claimed in claim 2, further comprising an amplifier having an input arranged to receive the output signal of the transducer and an output coupled to the analog input of the ADC.

5. The device as claimed in claim 4, further comprising an RF-to-DC converter arranged to power the analog-to-digital converter and the amplifier.

6. The device as claimed in claim 1, further comprising an RF-to-DC converter arranged to power active components in the device.

7. The device as claimed in claim 1, wherein the transponder is configured such that the electromagnetic signal received by the transponder and the electromagnetic signal re-radiated by the transponder oscillate at a common frequency.

8. The device as claimed in claim 1, wherein the transponder is configured such that an amplitude of the electromagnetic signal re-radiated by the transponder is modulated in response to the output signal of the transducer.

9. The device as claimed in claim 1, wherein:
    the transducer includes at least one ECG electrode adapted to sense ECG activity of the patient.

10. The device as claimed in claim 1, wherein the at least one transducer carrier includes at least one patch having an adhesive disposed thereon to permit the at least one patch to be secured to the external surface of the patient's skin.

11. A system for monitoring a physiological condition of a patient, comprising:
    a transmitter configured to emit an electromagnetic;
    a transducer adapted to sense the physiological condition of the patient at a location external to the patient's body and to produce an output signal indicative thereof;
    at least one transducer carrier, supporting the transducer, adapted to be secured to an external surface of the patient's skin;
    a transponder arranged to wirelessly receive the electromagnetic signal emitted by the transmitter and to re-radiate the electromagnetic signal, wherein the re-radiated electromagnetic signal is modulated in response to the output signal of the transducer; and
    a receiver configured to wirelessly receive the electromagnetic signal re-radiated by the transponder.

12. The system as claimed in claim 11, further comprising a demodulator, coupled to the receiver, configured to produce a demodulated signal by demodulating the electromagnetic signal received by the receiver.

13. The system as claimed in claim 12, further comprising means, responsive to the demodulated signal produced by the demodulator, for analyzing, processing or displaying the output signal of the transducer.

14. The system as claimed in claim 11, wherein the transponder is configured to re-radiate the electromagnetic signal such that an amplitude of the re-radiated electromagnetic signal is modulated in response to the output signal of the transducer.

15. The system as claimed in claim 11, further comprising an analog-to-digital converter (ADC) having an analog input coupled to an output of the transducer and a digital output coupled to the transponder to provide the transponder with a digital signal representative of the output signal of the transducer.

16. The system as claimed in claim 11, wherein:
    the transducer includes at least one ECG electrode adapted to sense ECG activity of the patient.

17. The system as claimed in claim 11, wherein the at least one transducer carrier includes at least one patch having an adhesive disposed thereon to permit the at least one patch to be secured to the external surface of the patient's skin.

18. A method for monitoring a physiological condition of a patient, comprising steps of:
    (a) sensing the physiological condition of the patient at a location external to the patient's body and producing an output signal indicative thereof;
    (b) wirelessly receiving an electromagnetic signal;
    (c) modulating the electromagnetic signal in response to the output signal to produce a modulated electromagnetic signal; and
    (d) re-radiating the modulated electromagnetic signal.

19. The method according to claim 18, wherein the step (c) includes steps of:

(c1) converting the output signal indicative of the physiological condition of the patient into a digital signal; and (c2) modulating the electromagnetic signal in response to the digital signal.

20. The method according to claim 19, wherein step (c2) includes a step of using the digital signal to selectively cause a diode coupled to an antenna included in the transponder to conduct, thereby modulating an amplitude of the electromagnetic signal.

21. The method according to claim 18, wherein:

the method further includes a step of (e) disposing at least one ECG electrode on an external surface of the patient's skin; and the step (a) includes a step of using the at least one ECG electrode to sense ECG activity of the patient.

22. A method for monitoring a physiological condition of a patient, comprising steps of:

using a transmitter to transmit an electromagnetic signal;

sensing the physiological condition of the patient at a location external to the patient's body and producing an output signal indicative thereof;

using a wireless device, distinct from the transmitter, to wirelessly receive the electromagnetic signal transmitted by the transmitter;

modulating the electromagnetic signal received by the wireless device in response to the output signal to produce a modulated electromagnetic signal;

using the wireless device to re-radiate the modulated electromagnetic signal; and using a receiver, distinct from the wireless device, to wirelessly receive the modulated electromagnetic signal.

23. The method according to claim 22, further comprising steps of:

demodulating the modulated electromagnetic signal received by the receiver to recover the output signal indicative of the physiological condition of the patient, and analyzing, processing or displaying the recovered output signal.

24. The method according to claim 22, wherein the step of modulating the electromagnetic signal includes steps of:

converting the output signal into a digital signal; and modulating the electromagnetic signal received by the wireless device in response to the digital signal.

25. The method according to claim 22, wherein:

the method further includes a step of disposing at least one ECG electrode on an external surface of the patient's skin; and the step of sensing the physiological condition of the patient includes a step of using the at least one ECG electrode to sense ECG activity of the patient.

* * * * *